(12) United States Patent
Iida et al.

(10) Patent No.: US 6,322,496 B1
(45) Date of Patent: Nov. 27, 2001

(54) ELECTRONIC ENDOSCOPE SYSTEM

(75) Inventors: Mitsuru Iida, Saitama-ken; Haruhiko Hibi, Tokyo, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/433,925

(22) Filed: Nov. 4, 1999

(30) Foreign Application Priority Data

Nov. 6, 1998 (JP) .................................................. 10-316015
Nov. 10, 1998 (JP) ................................................. 10-316301

(51) Int. Cl.⁷ .................................................. A61B 1/045
(52) U.S. Cl. ........................................... 600/118; 348/74
(58) Field of Search .................................. 6001/109, 118, 6001/101; 348/65, 71, 74

(56) References Cited

U.S. PATENT DOCUMENTS

| | | | |
|---|---|---|---|
| 5,609,560 | * 3/1997 | Ichikawa et al. | .................... 600/118 |
| 5,627,583 | * 5/1997 | Nakamura et al. | .................... 348/72 |
| 5,778,068 | * 8/1998 | Johnson et al. | .................... 713/189 |
| 5,902,230 | 5/1999 | Takahashi et al. | . |
| 6,037,858 | * 3/2000 | Seki | .................... 340/5.23 |

* cited by examiner

Primary Examiner—John P. Leubecker
(74) Attorney, Agent, or Firm—Greenblum & Bernstein, P.L.C.

(57) ABSTRACT

An electronic endoscope system includes an endoscope unit, a video processing unit, a display device. The video processing unit is provided with a device for changing parameters referred to for controlling illumination light and an image display condition. A registration ID (identification) code and the displaying parameters are stored in a nonvolatile memory. A hard key is detachably coupled to the video processing unit. The hard key stores an ID code intrinsic thereto, and the displaying condition is adjusted in accordance with the displaying parameters stored in the memory if the ID code of the hard key coincides with the registration ID code. While, the display condition is adjusted in accordance with a predetermined reference displaying parameters if the ID code of the hard key does not coincide with the registration ID code.

25 Claims, 14 Drawing Sheets

γ LEVEL  
   0.9 } D20

DIAPHRAGM STEP TABLE
| | |
|---|---|
| +5 | 10 |
| +4 | 05 |
| +3 | 04 |
| +2 | 07 |
| +1 | 09 |
| 0 | 03 |
| −1 | 06 |
| −2 | 03 |
| −3 | 08 |
| −4 | 12 |
| −5 | 25 |

} D21

SHUTTER SPEED  
   1/120 } D22

COLOR STEP  
   RED   12  
   GREEN 10  
   BLUE  08 } D23

ELECTRONIC ENDOSCOPE SYSTEM

BACKGROUND OF THE INVENTION

The present invention relates to an electronic endoscope system.

The electronic endoscope is generally provided with an endoscope unit, a main unit (a video signal processing unit), and a peripheral device including a display device.

The endoscope unit transmits light supplied from the main unit and illuminates a human body cavity. Further, the endoscope unit is provided with an image capturing device such as a CCD (Charge Coupled Device) for obtaining an image signal of the body cavity. In the endoscope unit, a signal processing circuitry is provided for processing image signals output by the CCD.

The main unit supplies illumination light as well as electrical power to the endoscope unit.

The peripheral device includes a CRT display for displaying the image obtained by the CCD, and a printer for outputting a hard copy thereof.

The main unit and the endoscope unit are connected through a connector. Electrical signals such as an image signal and transmitted from the circuitry in the endoscope unit to the main unit, and electrical power is supplied from the main unit to the endoscope circuitry through the connector. Further, the main unit and the peripheral devices are also connected through cables for transmitting electrical signals such as an image signal from the main unit to the peripheral devices.

A display condition of the displayed image, for example, a color balance thereof, contrast, and the like can be adjusted by performing predetermined operations such as signal processing operation in the main unit.

Settings of the image display is stored in a NVM (non-volatile memory) provided in the main unit, and such settings are maintained even if the main unit is powered OFF. The settings are retrieved when the main unit is powered ON next time, and an image is displayed in accordance with the retrieved settings.

In the above type of the endoscope system, when a plurality of operators use the same endoscope, a problem indicated below arises.

That is, when an operator used the endoscope system, adjusted the settings, and powered OFF the endoscope system, the adjusted setting were stored in the NVM. Thereafter, if another operator use the same endoscope system and changes the setting, then the changed settings will be stored when the endoscope is powered OFF. Thereafter, if the first operator powered ON the endoscope system again, the settings adjusted by the first operator are no more stored, and the setting made by the second operator are retrieved and made effective. In such a case, the first operator may consider the endoscope system malfunctions.

It is possible to configure the endoscope system not to store the settings adjusted by an operator. In such a case, an operator may not think the endoscope malfunctions. However, every operator must adjust the settings every time when he or she uses the endoscope system.

Further to the above, in the conventional electronic endoscope system another problem as indicated below may arise.

An operation of the endoscope system, for example, display of the image, is controlled in accordance with predetermined setting parameters.

Such setting parameters which are set during general operation, for example, a color balance of the display, a degree of enhancement of an image, can be done by switching an operation mode from a normal operation mode to a parameter setting mode.

Further, special setting parameters, for example, a gamma value, hue setting, can be set by changing the operation mode to a specific setting mode, which is different from the normal parameter setting mode. It is preferable that the special setting parameters should be changed only by authorized operators.

In the endoscope system configured as above, if the operation mode can easily be changed to the special parameters setting mode, an operator of the endoscope system may change the operation mode into the specific setting mode erroneously, and may change the specific setting parameters unintentionally.

To avoid such a situation, generally, the endoscope system is configured such that the operation mode cannot be changed to the specific setting mode until a predetermined specific operation, which cannot be performed easily, is executed. For example, in order to change the operation mode to the specific parameter setting mode, a ROM storing the special parameters is provided in a housing of the main unit is to be replaced with another ROM for maintenance work. Only when the ROM is replaced, the CPU changes the operation modes in accordance with the data stored in the ROM.

In the above type of the electronic endoscope system, in which an operator is required to perform a predetermined operation to change the operation mode from the normal setting mode to the specific parameter setting mode, although the erroneous operation is prevented, when the specific mode is to be selected, it is necessary to open the housing and the circuit board accommodated in the housing should be taken out. Such an operation is troublesome and time consuming.

SUMMARY OF THE INVENTION

In view of the above problem in the conventional electronic endoscope system, it is an object of the present invention to provide an improved electronic endoscope system, in which, each of a plurality of operators can change the setting parameters easily, and for each operator, the previous setting parameters are retrieved easily.

Another object of the present invention is to provide an improved electronic endoscope system, in which erroneous switching of operation mode into a specific parameter setting mode can be prevented, and further, when necessary, the mode can be switched to the specific parameter setting mode quickly.

According to an aspect of the invention, there is provided an electronic endoscope system that includes an endoscope unit provided with an image capturing device, the image capturing device outputting an image signal representing a captured image; a video processing unit for processing the image signal output by the image capturing device; and a display device that displays an image in accordance with the image signal processed by the video processing unit.

In such an electronic endoscope system, the video processing unit including: an image display condition controlling system that controls a displaying condition of an image on the display device. The displaying condition is determined in accordance with displaying parameters. A changing device is further provided for changing the displaying parameters, and a memory is also provided for storing at least one registration ID (identification) code and the displaying parameters.

The endoscope system further includes an ID code input member, which inputs an ID code intrinsic to the ID code input member, to the video processing unit.

The video processing unit further includes a discriminating system which discriminates whether the ID code input from the ID code input member coincides with the at least one registration ID code; a controller that controls the display condition controlling system to adjust the displaying condition in accordance with the displaying parameters stored in the memory when the ID code input from the ID code input member coincides with the at least one registration ID code, the controller controlling the display condition controlling system to adjust the displaying condition in accordance with a predetermined reference displaying parameters when the ID code input from the ID code input member does not coincide with the at least one registration ID code.

Optionally, the controller may control the image display condition controlling system to adjust the displaying condition in accordance with the predetermined reference displaying parameters when the ID code is not input from the ID code input member.

The controller may store the displaying parameters set in the display condition controlling system in the memory when the ID code input from the ID code input member coincides with the at least one registration ID code. Optionally, the controller may store the display parameters in the memory when the displaying parameters are changed by the changing device.

Further optionally, the ID code input member comprises a hard key which stores an ID code assigned thereto. The video processing unit further includes a communication system which is detachably coupled to the hard key, and the discriminating system transmits a request via the communication system to the hard key for response, the hard key transmits the ID code storing therein to the discrimination system via the communication system in response to the request.

In this case, the controller may control the image display condition controlling system to adjust the displaying condition in accordance with predetermined reference displaying parameters when the communication system does not receive a response from the hard key.

Optionally, the display condition parameters may include at least one of a parameter for setting color balance of an image and a parameter for setting an enhancement of a displayed image.

Still optionally, the electronic endoscope system may includes a light source for emitting light, and a light guide cable for directing the light emitted by the light source to the endoscope unit. The display condition parameters may include a parameter for setting light amount, and the controller controls the amount of light guided by the light guide cable in accordance with the parameter for setting light amount.

According to another aspect of the invention, there is provided an electronic endoscope system, including an endoscope unit provided with an image capturing device, the image capturing device outputting an image signal representing a captured image; a video processing unit for processing the image signal output by the image capturing device; and a display device that displays an image in accordance with the image signal processed by the video processing unit, and the video processing unit may include:

an image display condition controlling system that controls a displaying condition of an image on the display device, the displaying condition being determined in accordance with displaying parameters; a changing device for changing the displaying parameters; a memory for storing a plurality of registration ID (identification) codes and a plurality of sets of displaying parameters, the plurality of sets corresponding to the plurality of registration ID codes, respectively. The endoscope system may further includes an ID code input member, which inputs an ID code intrinsic to the ID code member, to the video processing unit.

The video processing unit further includes: a discriminating system which discriminates whether the ID code input from the ID code input member coincides with one of the plurality of registration ID codes; and a controller that controls the display condition controlling system to adjust the displaying condition in accordance with one of the plurality of sets of displaying parameters stored in the memory and corresponding to the ID code input from the ID code input member when the ID code input from the ID code input member coincides with one of the plurality of sets of registration ID codes, the controller controlling the display condition controlling system to adjust the displaying condition in accordance with predetermined reference displaying parameters when the ID code input from the ID code input member does not coincide with any one of the plurality of registration ID codes.

Optionally, the controller controlling the display condition controlling system to adjust the displaying condition in accordance with the predetermined reference displaying parameters when the ID code is not input from the ID code input member.

Further, the controller stores the displaying parameters set in the display condition controlling system in the memory in relation to a registration ID code which coincides with the ID code input from the ID code input member when the ID code input from the ID code input member coincides with the one of the plurality of registration ID codes.

Still optionally, the controller stores the display parameters in the memory when the displaying parameters are changed by the changing device.

In particular, the ID code input member may include a hard key to which stores an ID code assigned thereto, the video processing unit further includes a communication system which is detachably coupled to the hard key, wherein the discriminating system transmits a request via the communication system to the hard key for response, and the hard key transmits the ID code storing therein to the discrimination system via the communication system in response to the request.

In this case, the controller may control the image display condition controlling system to adjust the displaying condition in accordance with predetermined reference displaying parameters when the communication system does not receive a response from the hard key.

Further optionally, the display condition parameters include at least one of a parameter for setting color balance of an image and a parameter for setting an enhancement of a displayed image.

Still optionally, the endoscope system may include a light source for emitting light, and a light guide cable for directing the light emitted by the light source to the endoscope unit, the display condition parameters include a parameter for setting light amount, the controller controls the amount of light guided by the light guide cable in accordance with the parameter for setting light amount.

According to a further aspect of the invention, there is provided an electronic endoscope system which operates in accordance with setting information, the setting information including at least first setting parameters and second setting parameters, the electronic endoscope system operable either in a first setting mode where the first setting parameters are changed or in a second setting mode where the second setting parameters are changed, the electronic endoscope system provided with: a memory for storing a registration ID (identification) code; an ID code input member stores an ID code intrinsic to the ID code input member, a discriminating system, the ID code intrinsic to the ID code input member being input to the discriminating system, the discriminating system discriminating whether the ID code received from the ID code input member coincides with the registration ID code; and a controller that allows the endoscope system to operate in the second setting mode only when the discriminating system has received the ID code from the ID code input member and the ID code coincides with the registration ID code.

Optionally, the controller may control the endoscope system to operate in the second setting mode when the discriminating system has received the ID code from the ID code input member and the ID code coincides with the registration ID code.

Further optionally, the endoscope unit may include a display device, and wherein the setting information includes display condition setting parameters for setting a display condition of an image on the display device.

In particular, the ID code input member may include a hard key which stores an ID code assigned thereto, discriminating system further comprising a communication system to which the hard key is detachably coupled, wherein the communication system transmits a request to the hard key for response, and the hard key transmits the ID code storing therein to the communication system in response to the request.

Further, the controller may inhibit the electronic endoscope system from operating in the second setting mode when the communication system does not receive a response from the hard key.

Optionally, the first setting parameters include at least one of a parameter for setting color balance of an image and a parameter for setting an enhancement of a displayed image.

Further optionally, the endoscope system may include a light source for emitting light, and a light guide cable for directing the light emitted by the light source to the endoscope unit. The display condition setting parameters include a parameter for setting light amount, and the controller controls the amount of light guided by the light guide cable in accordance with the parameter for setting light amount.

In particular, the second setting parameters includes at least one of a game level setting parameter for setting gamma correction level for the display and a parameter for setting hue of a displayed image.

Further optionally, the endoscope system may include an endoscope unit provided with an image capturing device, and the second setting parameters include a parameter for setting a shutter speed for the image capturing device.

BRIEF DESCRIPTION OF THE ACCOMPANYING DRAWINGS

Figure 5:
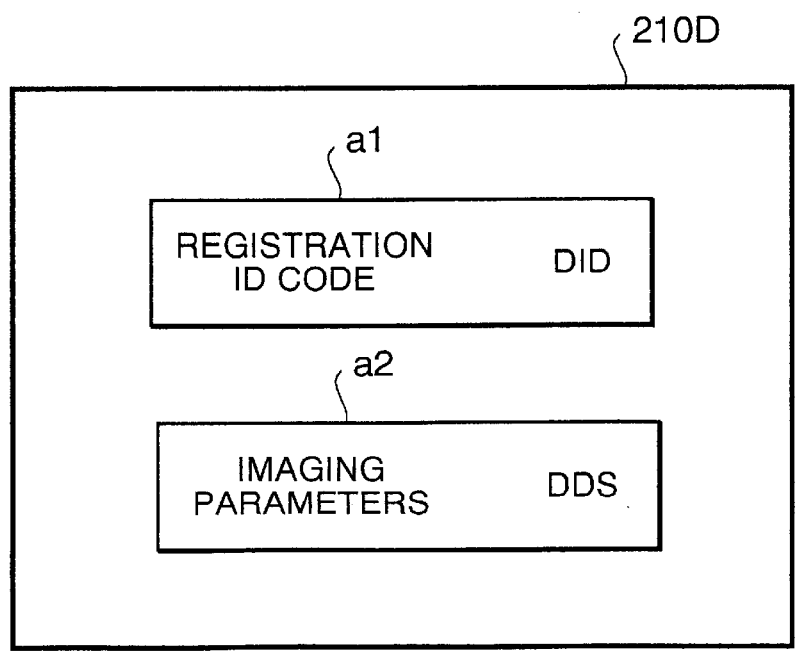
Figure 6:
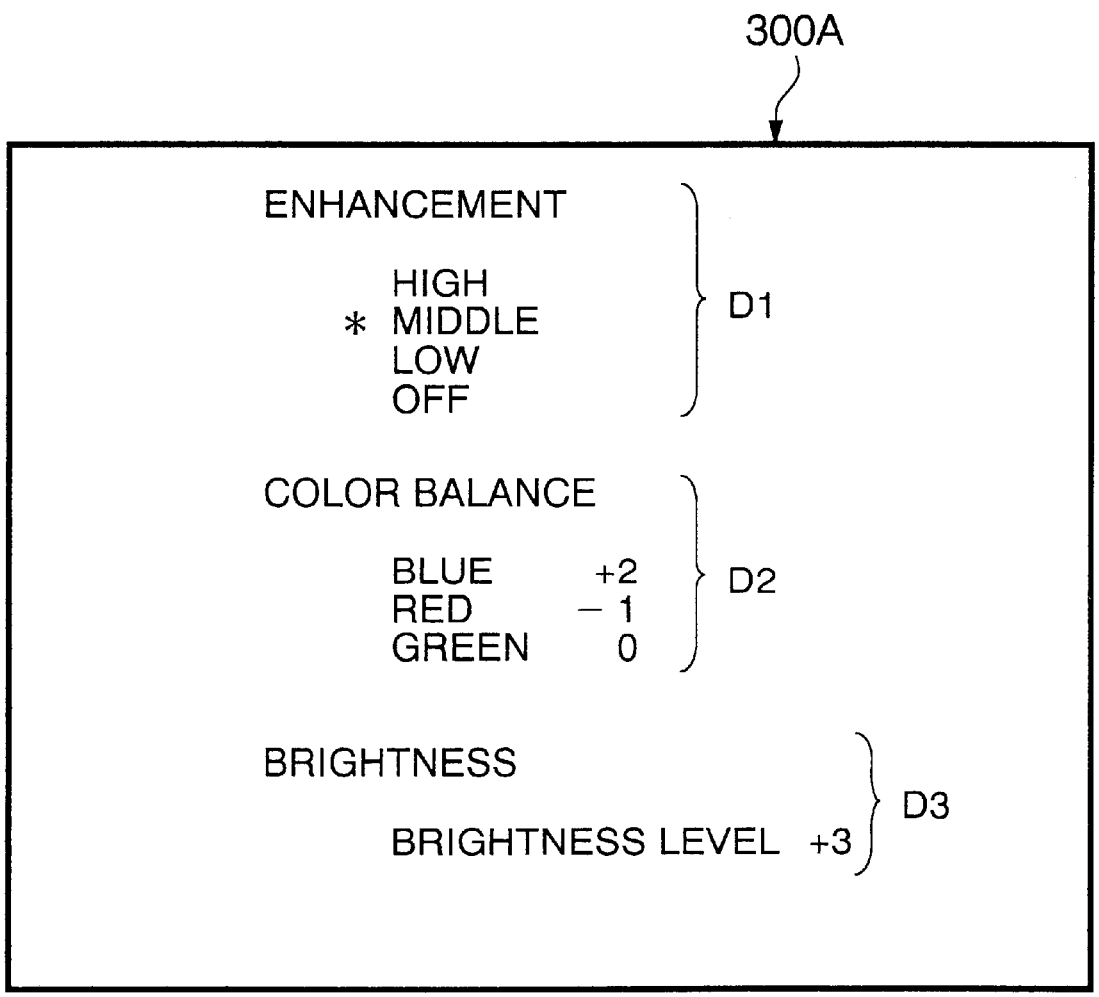
Figure 7:
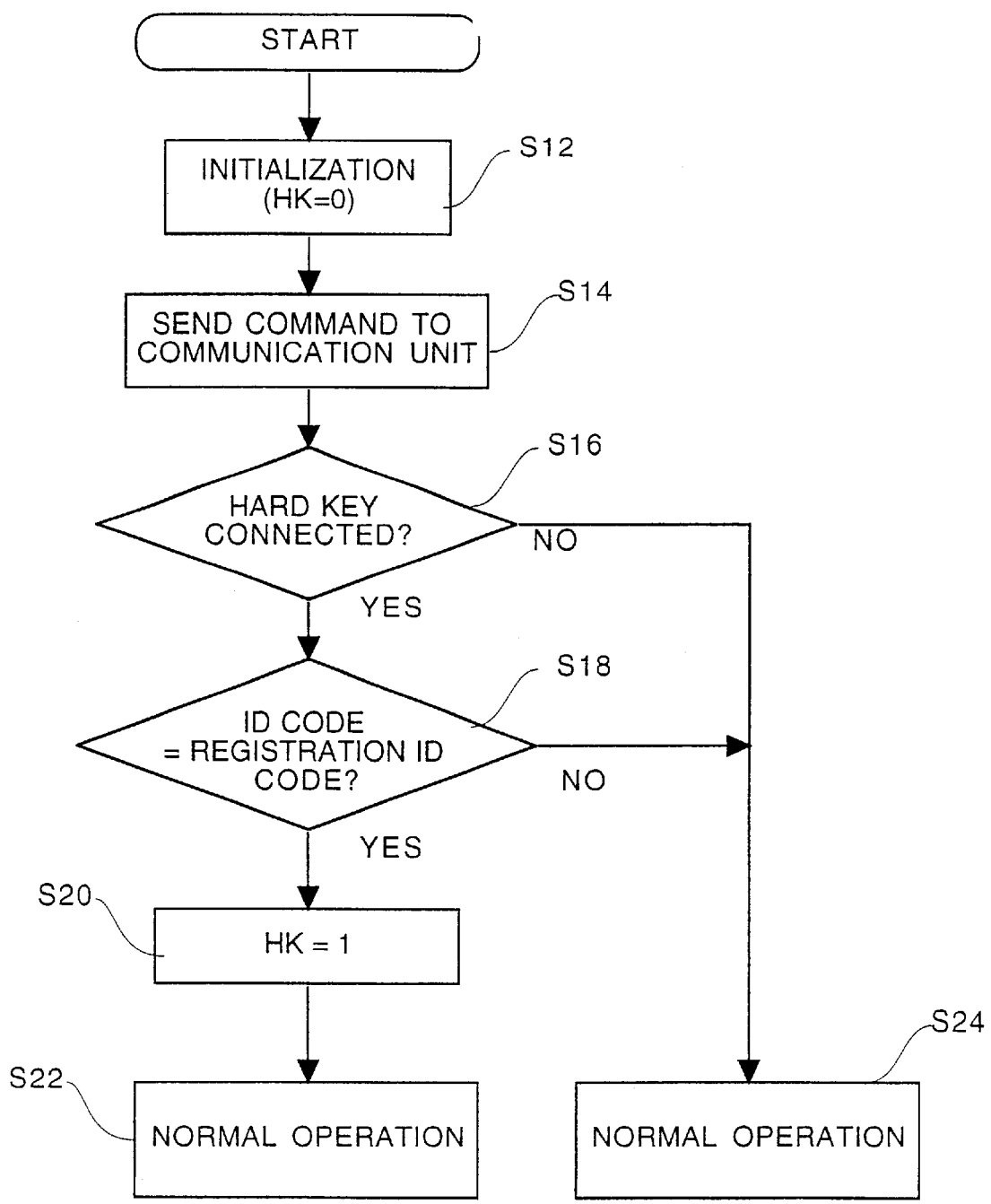
Figure 8:
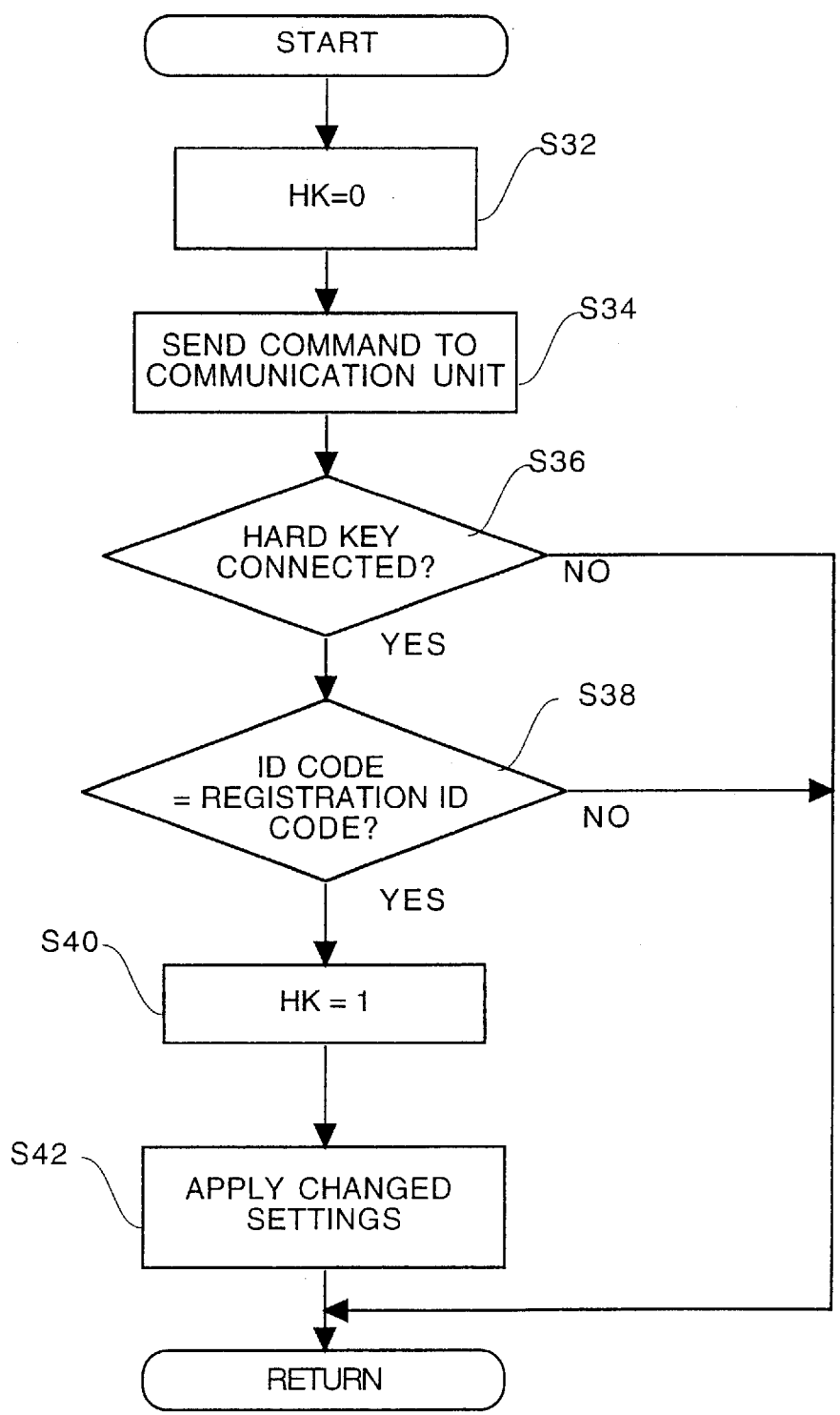
Figure 9:
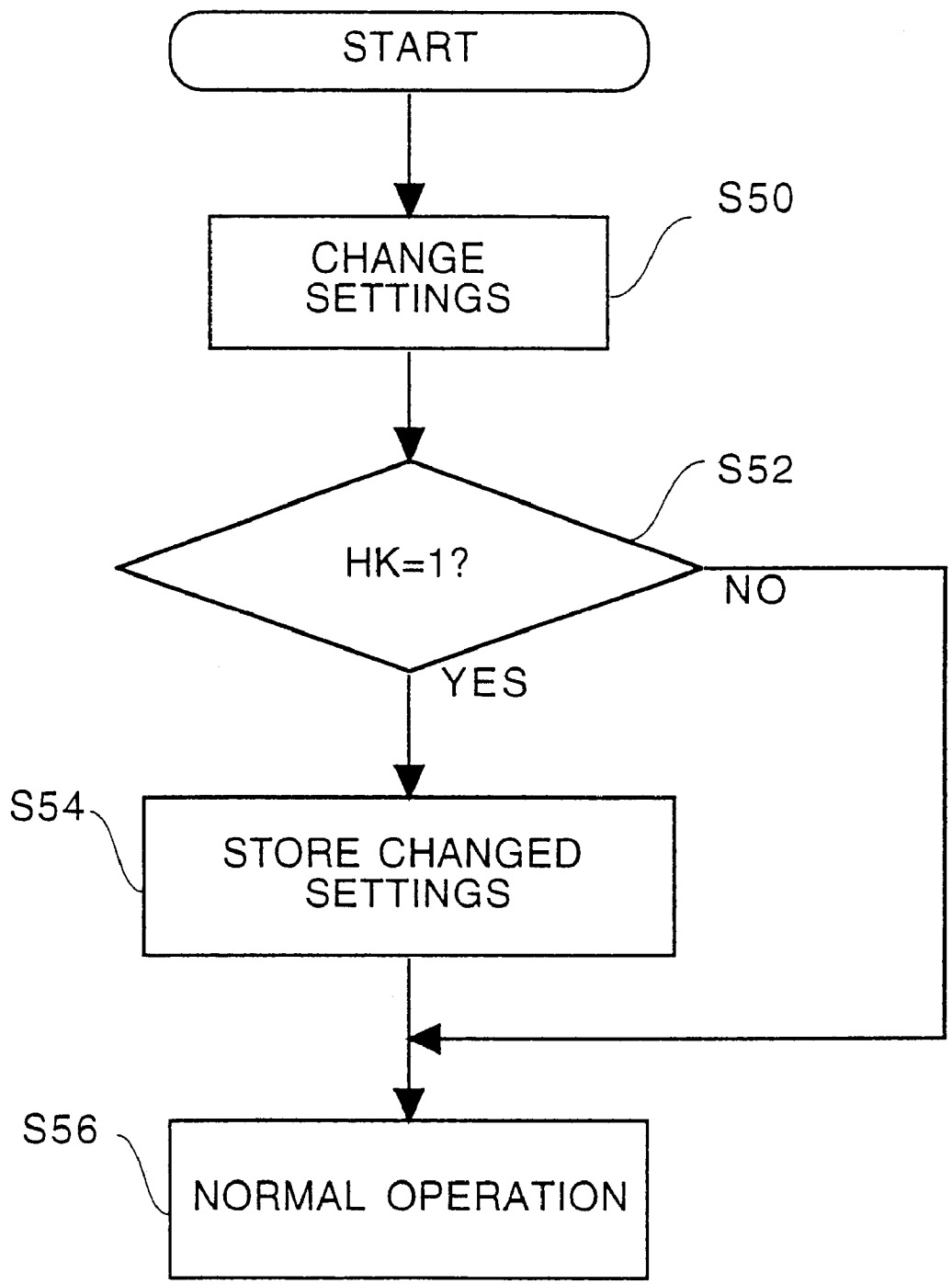
Figure 10:
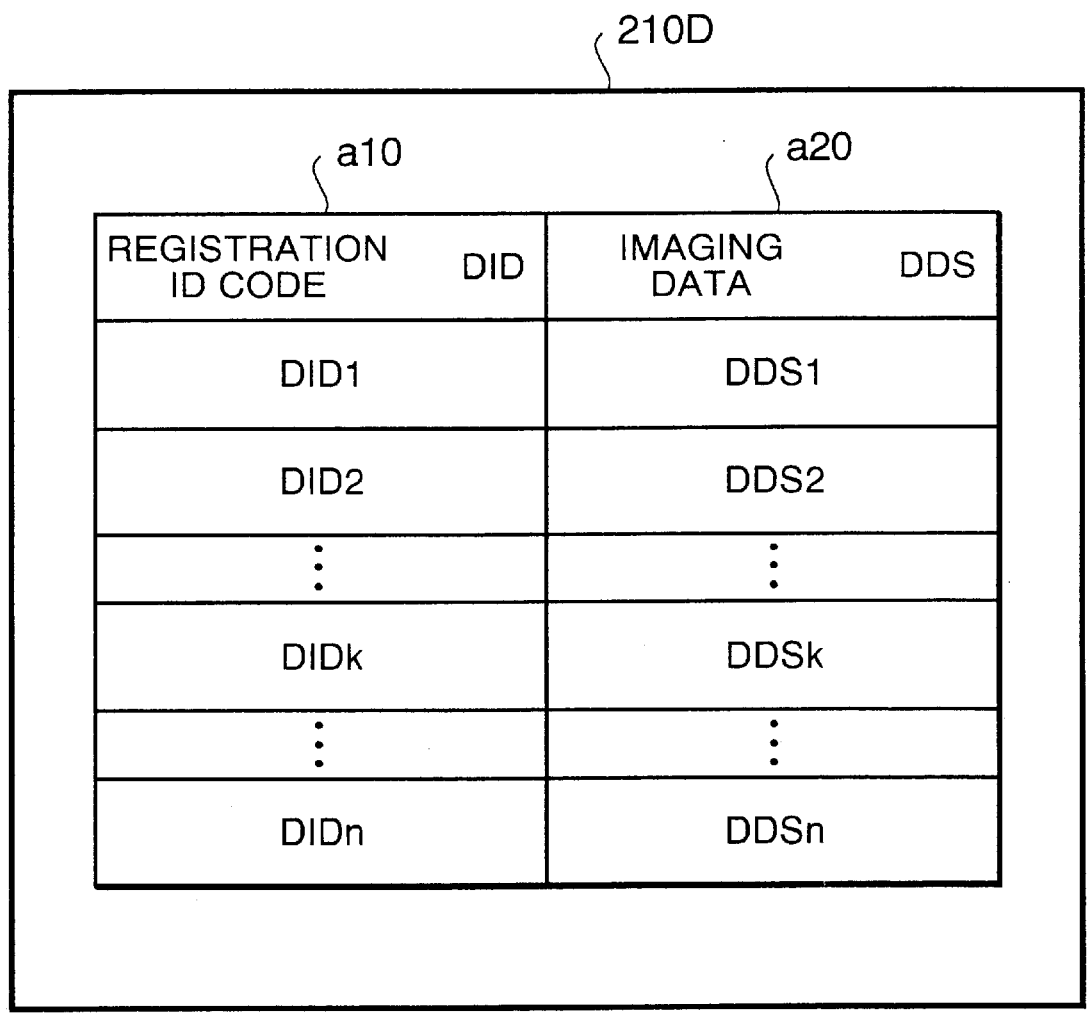
Figure 11:
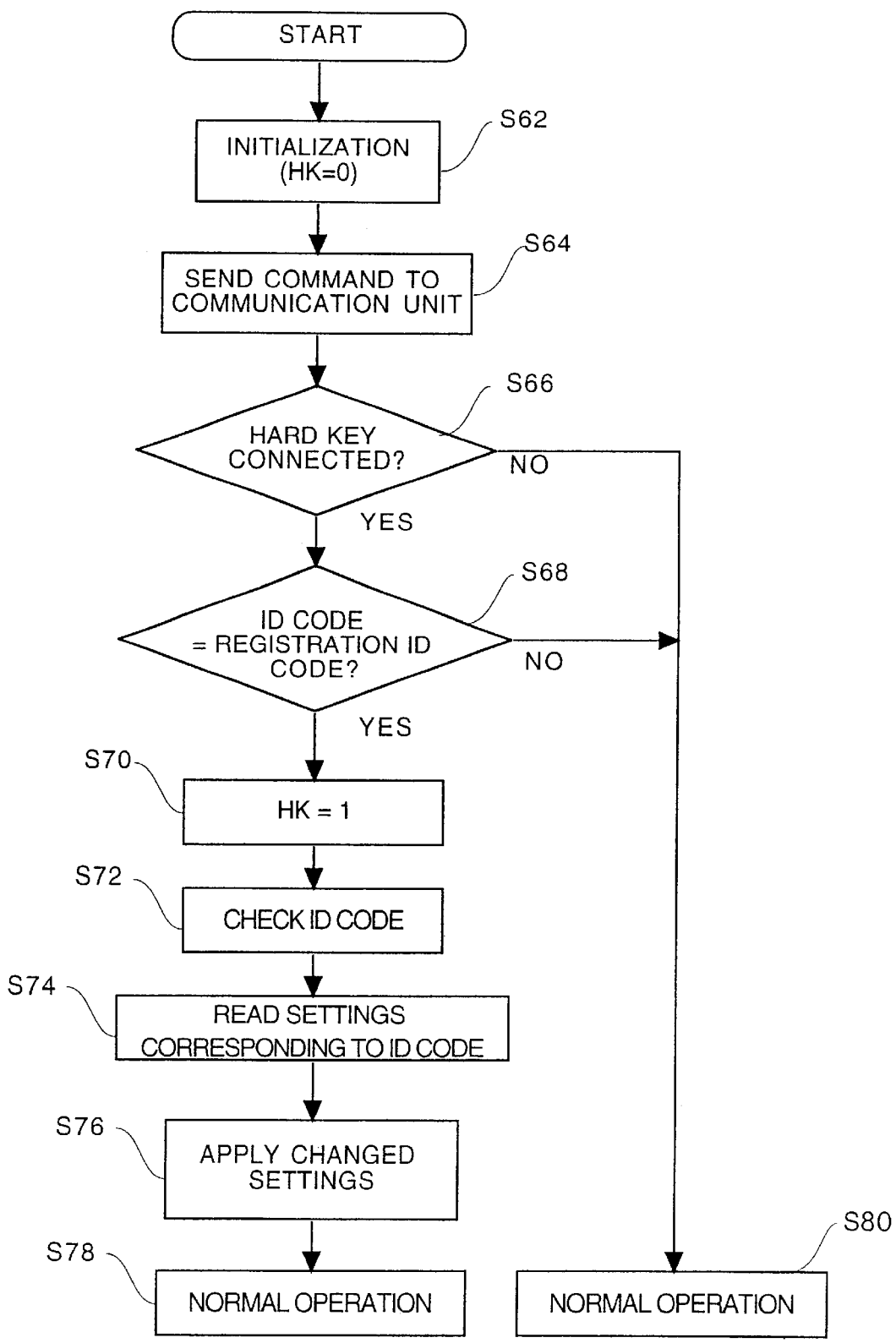
Figure 12:
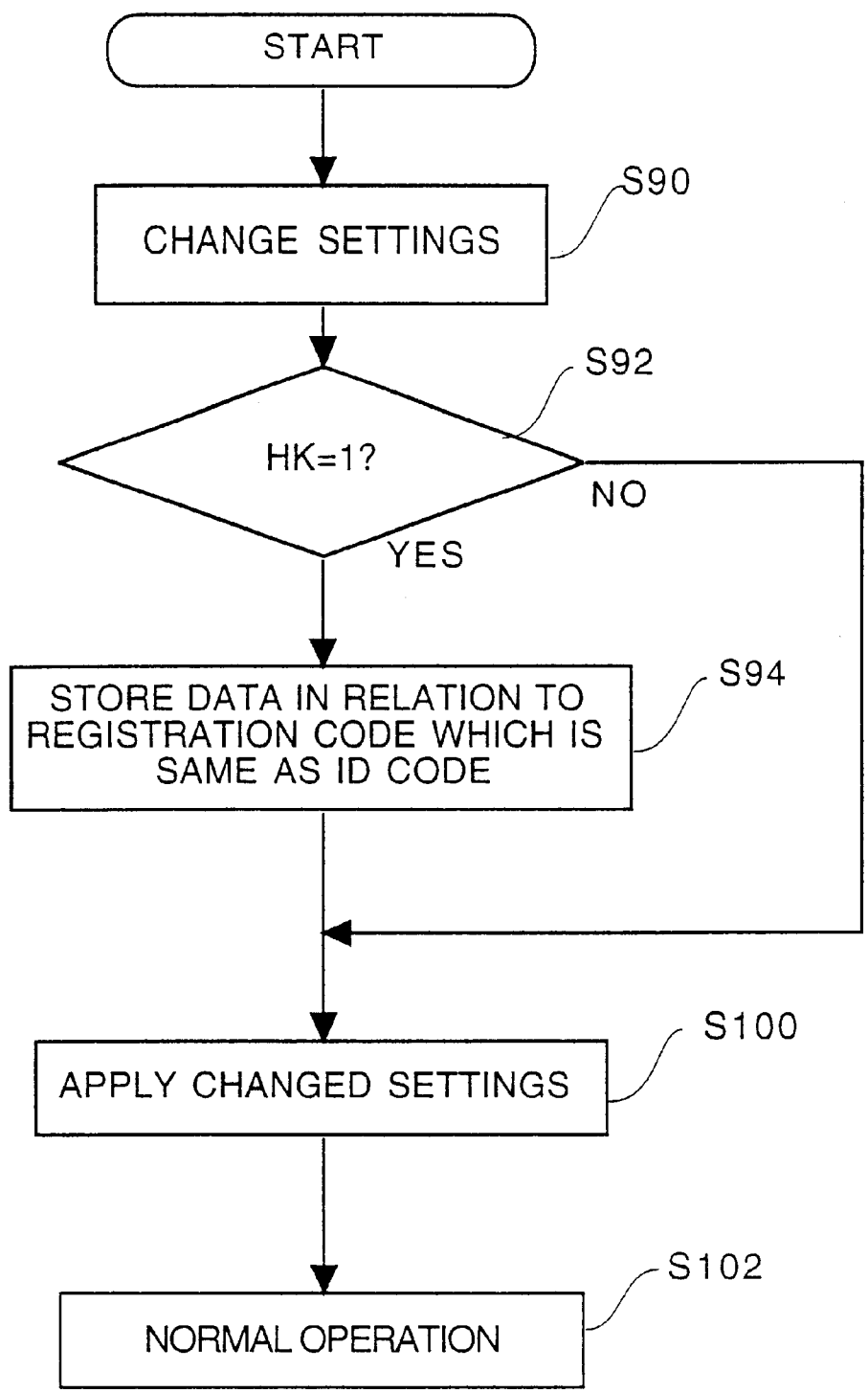
Figure 13:
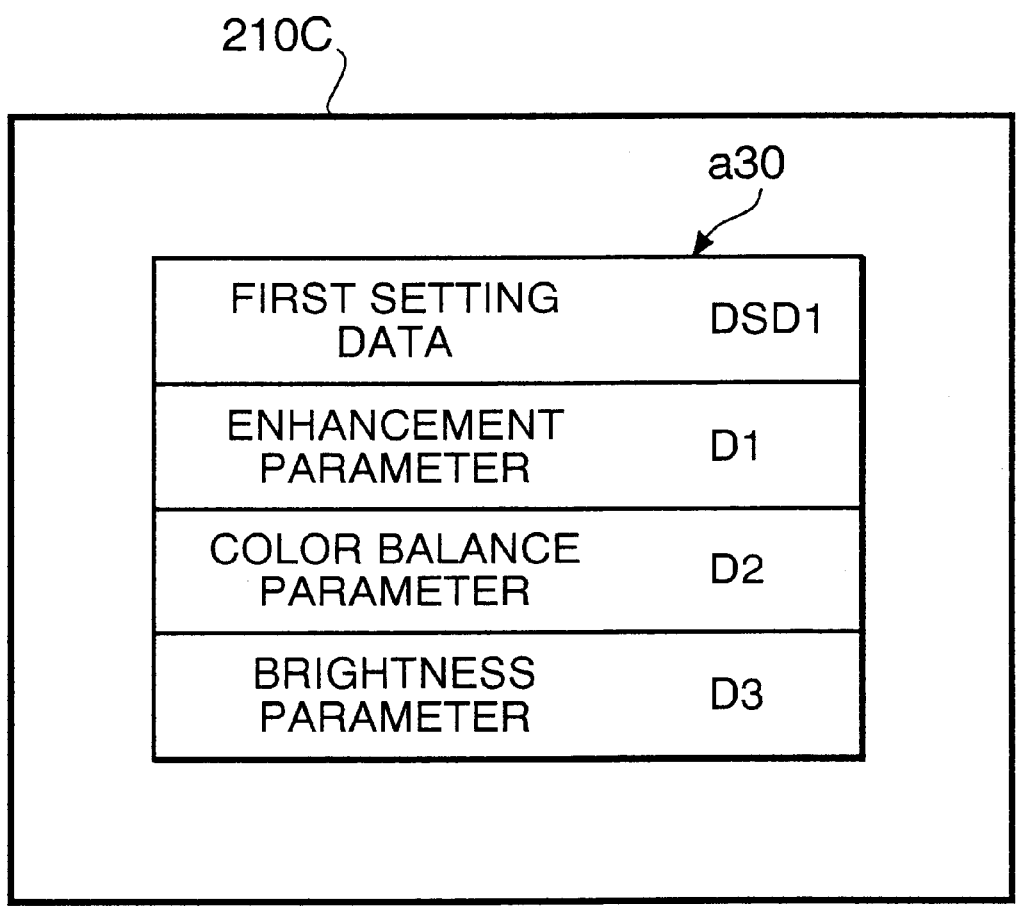
Figure 14:
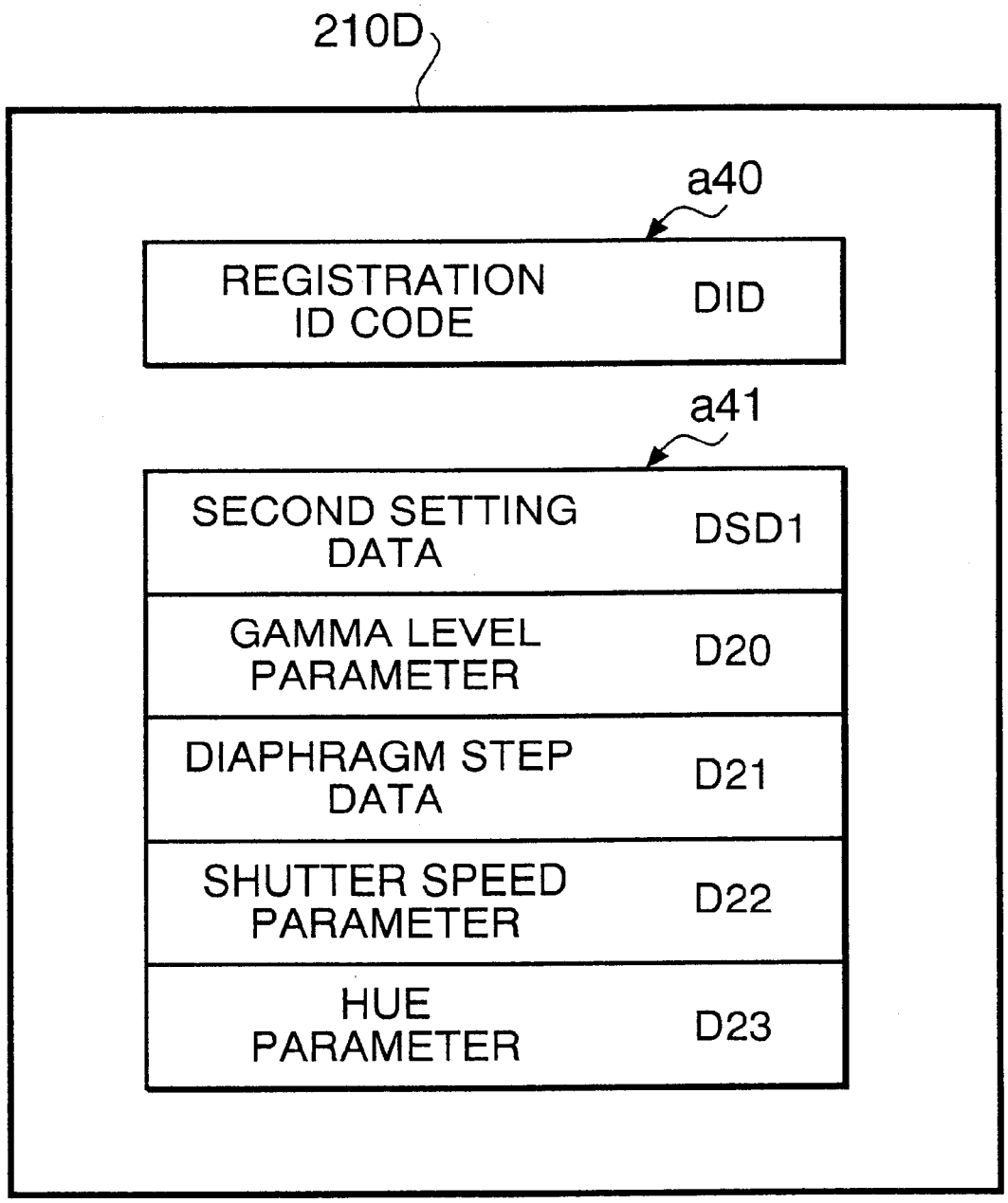

FIG. 5 schematically illustrates storage areas in a battery back up RAM;

FIG. 6 shows an exemplary screen image when image display parameters are changed;

FIG. 7 is a flowchart showing a main procedure according to a first embodiment;

FIG. 8 is a flowchart showing a subroutine for monitoring whether a hard key is connected during a normal operation;

FIG. 9 is a flowchart showing a parameter changing operation;

FIG. 10 schematically shows storage areas of a battery back up RAM according to a second embodiment;

FIG. 11 is a flowchart showing a main procedure according to the second embodiment;

FIG. 12 is a flowchart showing a parameter changing operation according to the second embodiment;

FIG. 13 schematically shows data storage areas in a RAM according to a third embodiment;

FIG. 14 schematically shows data storage areas in a battery back up RAM according to the third embodiment;

FIG. 15 shows a screen image when special setting parameters are changed; and

Figure 16:
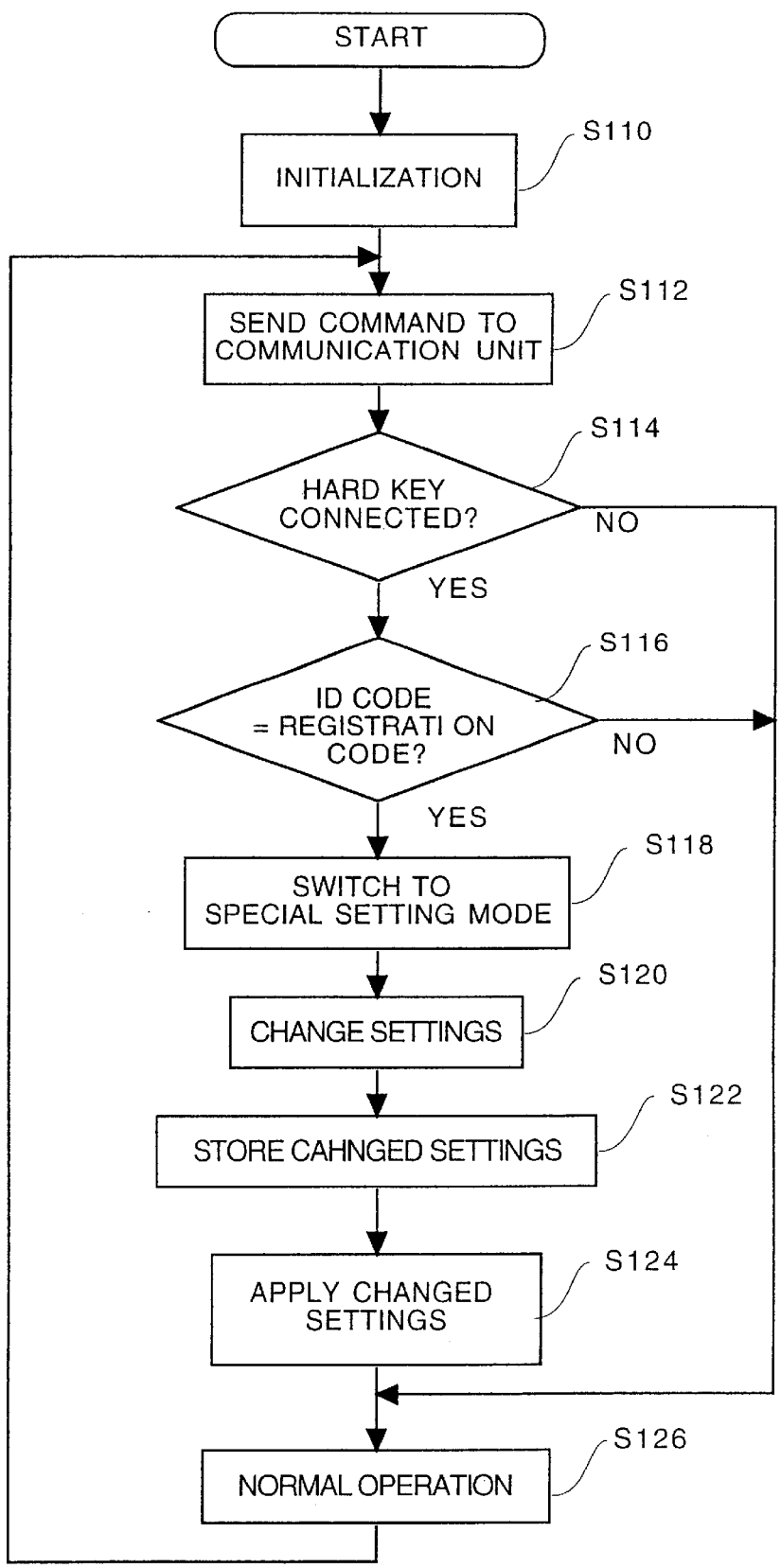

FIG. 16 is a flowchart illustrating a main procedure according to a third embodiment.

DESCRIPTION OF THE EMBODIMENTS

Hereinafter, the present invention will be described with reference to the accompanying drawings.

Figure 1:
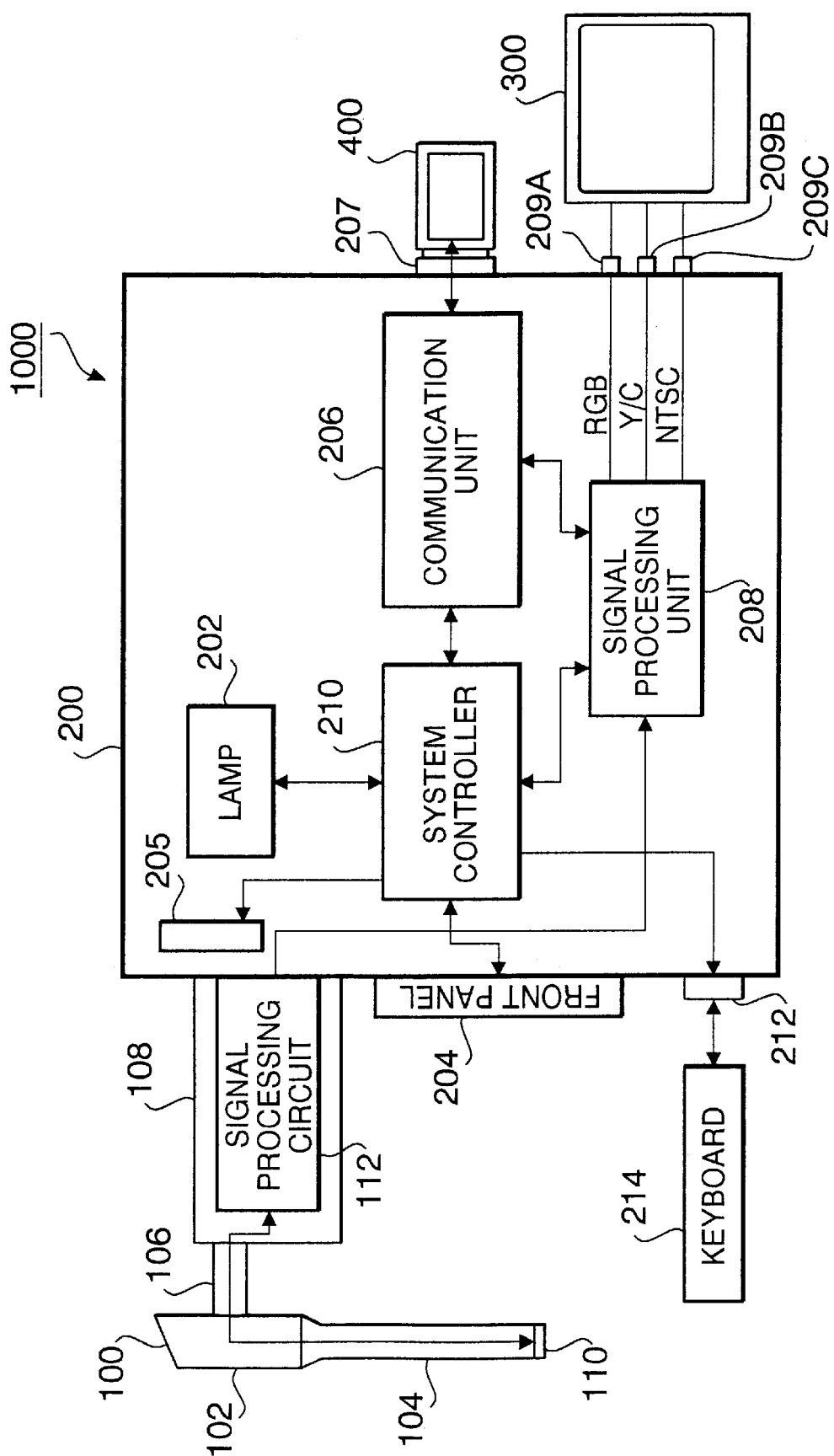
FIG. 1 is a block diagram showing a control system of an electronic endoscope system embodying the present invention.

FIG. 1 is a block diagram showing a control system of an electronic endoscope system 1000 embodying the present invention. The electronic endoscope system 1000 includes an endoscope unit 100, a main unit 200, a display device 300, and a hard key 400.

The endoscope unit 100 includes an operation section 102 to be operated by an operator, a flexible tube 104 which is projected from the operation section 102 and inserted in a body cavity of a patient, a lamp guide cable 106 which is projected from another side of said operation section 102. At the end portion of the lamp guide cable 106, a connector unit 108 to be coupled to the main unit 200 is provided.

At a distal end of the flexible tube, a CCD (Charge Coupled Device) 110 is provided. In the connector unit 108, a signal processing circuit 112 which drives the CCD 110 and processes an image signal output by the CCD 110 is provided.

The connector unit 108 transmits the image signal output by the signal processing circuit 112 to a signal processing unit 208 in the main unit 200 when coupled to the main unit 200. Further, the connector unit 108 transmits power supplied by the main unit 200 to the signal processing circuit 112. Further, The connector unit 108, when coupled to the main unit 200, includes an optical connector section which directs the light emitted by a lamp 202 accommodated in the main unit 200 to the lamp guide cable 106.

The main unit 200 is provided with the lamp 202, a front panel 204, a communication unit 206, the signal processing unit 208, and a system controller 210.

As described above, the lamp 202 is a light source for supplying light to the endoscope unit 100. In the first embodiment, the light source is provided in the main unit 200. The light source can be provided separately from the main unit 200.

Between the lamp 202 and the optical connector for directing the light emitted by the lamp 202 to the light guide cable 106, an aperture mechanism 205 is provided for adjusting the amount of light incident on the light guide cable 106. Such an aperture mechanism 205 may operate in accordance with a control signal transmitted by the system controller 210.

The front panel 204 has a touch panel consisting of a display window and touch switches provided on the display window. By operating the touch switches, an operation signal is generated and transmitted to the system controller 210. In accordance with the control signal transmitted from the system controller 210, information necessary for operation is displayed on the touch panel.

The communication unit 206 is connected to a connector 207, and performs a communication operation with a hard key 400 connected to the connector 207. It should be noted that the connector may be a communication port generally used for connecting the endoscope with an external device such as a personal computer.

The signal processor 208 receives the image signal from the signal processing circuit 112, and generates an ROB signal, a Y/C signal, an NTSC signal and the like. Such signals are output through connectors 209A, 209B and 209C. The display device 300 is connected to one of the connectors 209A, 209B or 209C, and displays an image in accordance with the signal received through the connected connector.

To the main unit 200, a keyboard 214 is detachably connected via a connector 212. By inputting operation commands through the keyboard 214, operations which can be initiated using the front panel 208 can also be instructed.

Figure 2:
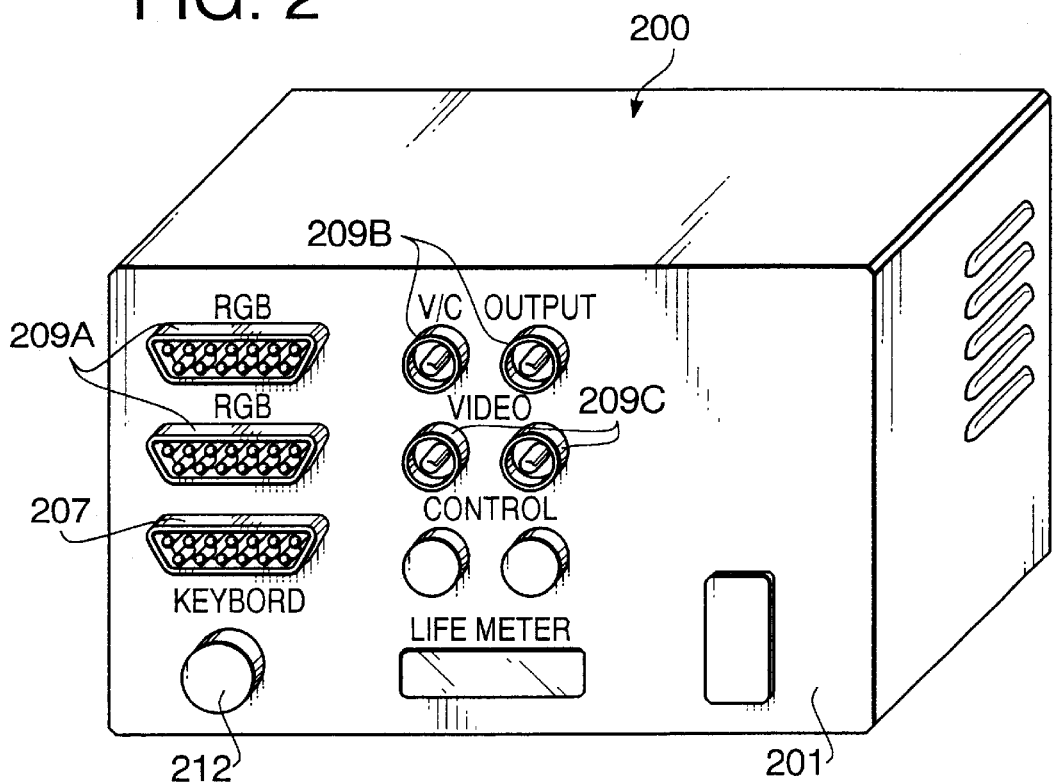
FIG. 2 is a perspective rear view of a main unit of the endoscope system.

FIG. 2 is a perspective rear view of the main unit 200 of the endoscope system 100. As shown in FIG. 2, on a rear panel 201, the connectors 207, 209A–209C and 212 are provided.

Figure 3A:
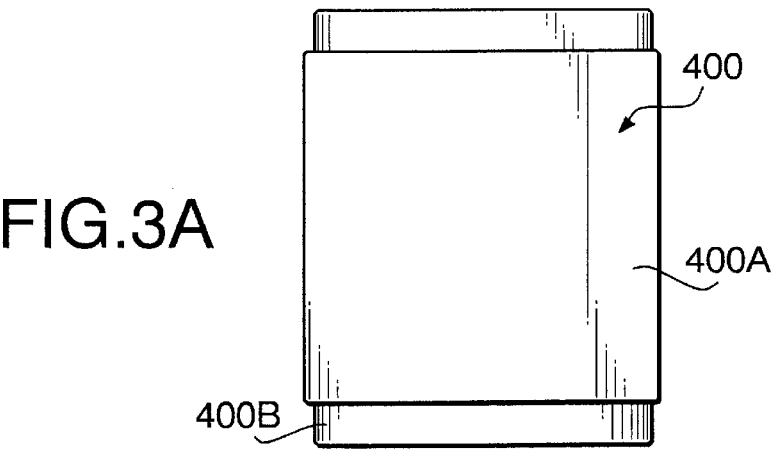
FIG. 3A is a plan view of a hard key.
Figure 3B:
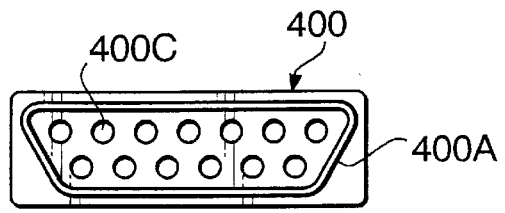
FIG. 3B is a front view of the hard key.

FIG. 3A is a plan view, and FIG. 3B is a front view of the hard key 400. As shown in FIGS. 3A and 3B, the hard key 400 has a casing 400A whose shape is a flat rectangular solid. On one side end surface of the casing 400A, a connector 400B to be coupled to the connector 207 of the main unit 200 is provided. The connector 400B has a plurality of terminals 400C. Inside the casing 400A, a microcomputer is provided, which communicates with the communication unit 206 via the connectors 400B and 207. The microcomputer stores a predetermined ID (Identification) code assigned to the hard key 400.

Figure 4:
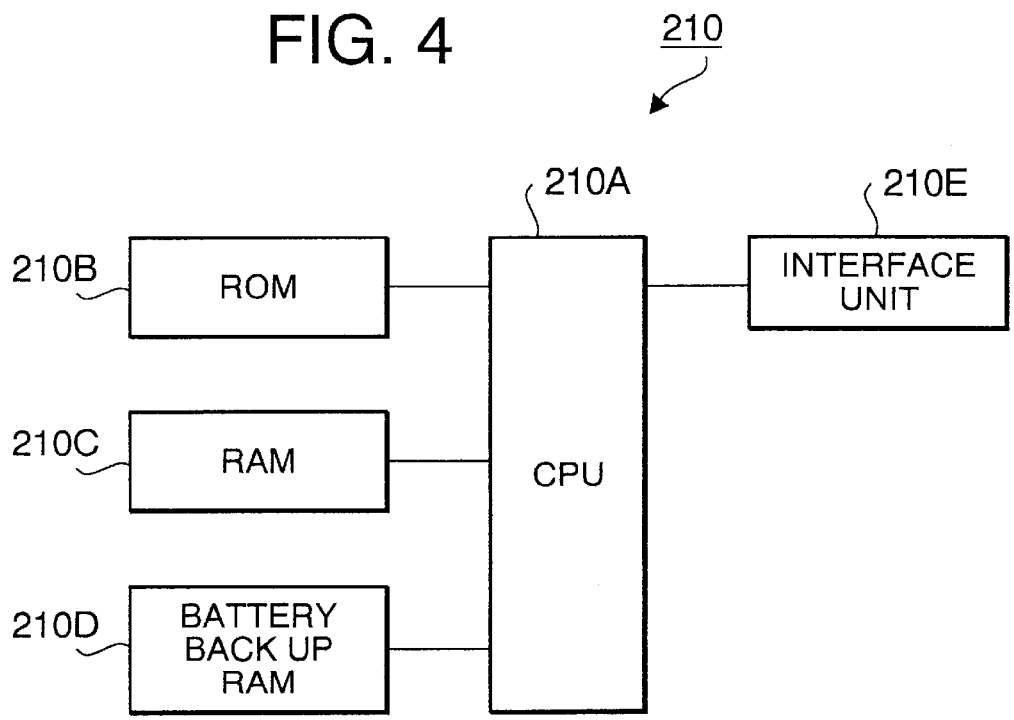
FIG. 4 is a block diagram of a system control unit.

FIG. 4 is a block diagram of a system controller 210. The system controller 210 includes a CPU 210A, a ROM 210B, a RAM 10C, a battery back up RAM 210D, and an interface unit 210E.

The RAM 210D stores control programs executed by the CPU 210A. The RAM 210C is mainly used as a work area when the programs are executed by the CPU 210A. The battery back up RAM 210D stores a registration ID code and imaging parameters (which will also be referred to as imaging data), and holds data (i.e., the ID code and the imaging parameters) even if the power of the main unit 200 is turned OFF. Further, the data stored in the battery back up RAM 210D can be rewritten. The interface unit 210E is configured to exchange signals and data with the lamp 202, front panel 204, the keyboard 214, and the signal processing unit 208.

First Embodiment

FIG. 5 schematically illustrates data stored in a battery back up RAM 210D according to a first embodiment. As shown in FIG. 5, the battery back up RAM 210D has a first storage area a1 for storing the registration ID code DID, and a second storage area a2 for storing imaging data (i.e., imaging parameters) DDS.

The registration ID code represents an ID code assigned to a specific operator operating the electronic endoscope system 1000. The specific operators having the hard key 400 which stores the same data as the registration ID code DID. When the hard key 400 is coupled to the connector 207 of the main unit 200, the ID code stored in the hard key 400 is transmitted to the communication unit 206.

The imaging data DDS represents parameters for setting an image displaying condition on the display device 300 and the light amount of the lamp 202.

FIG. 6 shows an exemplary screen image 300A on the display device 300 when the imaging parameters are to be changed. The image as shown in FIG. 6 is displayed when the main unit 200 operates in a parameter changing mode, which is selected by executing a predetermined operation using the touch switches of the front panel 204.

As shown in FIG. 6, on a display screen 300A of the display device 300, changeable parameters and settings of each parameter are displayed. In FIG. 6, as the changeable parameters, menu items "Enhancement", "Color Balance" and "Brightness" are displayed. The menu item "Enhancement" relates to enhancement parameter D1 which represents a degree of enhancement of an image displayed on the display device 300. The item "Color Balance" relates to color balance parameter D2 which represents a degree of the color balance effect on the display device 300. The item "Brightness" is a brightness parameter D3 representing the amount of light directed from the lamp 202 to the light guide cable 106 (i.e., the size of an aperture defined by the aperture mechanism 205).

In the example shown in FIG. 6, the enhancement parameters D1 includes four settings: "High"; "Middle"; "Low"; and "Off", and "Middle" setting is currently selected. The color balance parameter D2 includes three sub-items, "Blue", "Red" and "Green", each of which is set with a value. The brightness parameter D3 includes a brightness level setting which can also be set with a value. The selection of the items, sub-items, settings and values can be done using the touch switches of the front panel 204 of the main unit 200. The changed settings are temporarily stored in the RAM 210C.

The system controller 210 controls the signal processing unit 208 so that an image is displayed on the display device 300 in accordance with the enhancement parameter D1 and the color balance parameter D2 stored in the RAM 210C. Further, the system controller 210 controls the aperture mechanism 205 in accordance with the brightness parameter D3 to change the aperture size of the aperture mechanism stepwise so that the amount of light emitted by the lamp 202 and directed to the light guide cable 106 is changed.

It should be noted that, as default values, reference settings of the enhancement, color balance and brightness parameters are stored in the ROM 210B.

FIG. 7 is a flowchart illustrating a main procedure of the electronic endoscope system 1000 according to the first embodiment. The main procedure starts when a main switch (not shown) of the main unit 200 is turned ON, and power is supplied to circuits therein.

When the main unit 200 is powered ON, the CPU 210A performs an initialization operation (S12), during which a variable HK stored in the RAM 210C is set to zero (0). The variable HK represents presence/absence of the hard key 400. That is, when the hard key 400 is not connected, the variable HK equals 0, while when the hard key 400 has been connected, the variable HK equals 1.

In S14, the system controller 210 sends a command to the connector unit 206 to detect whether the hard key 400 is coupled to the connector 207. In response to reception of the command, the communication unit 206 transmits a signal to the connector 207 requiring to respond. Based on the absence/presence of the response from the hard key 400 via the connector 207, the communication unit 206 determines whether the hard key 400 is coupled to the connector 207 (S16).

If the hard key 400 responds, the communication unit 206 communicates with the hard key 400 to receive the ID code stored in the hard key 400, and transmits the received ID code to the system controller 210.

In S18, the system controller 210 determines whether the ID code transmitted from the hard key 400 is correct, i.e., the ID code coincides with the registration ID code stored in the battery back up RMA 210D. If the ID code received from the hard key 400 coincides with the registration ID code stores in the battery back up RAM 210D (S18: YES), the variable HK is set to 1 (S20), which represents the hard key 400 is coupled to the connector 207.

Then, the CPU 210A executes a normal operation, i.e., the CPU 210A controls, in accordance with the imaging parameters DDS stored in the battery back up RAM 210D, the signal processing unit 208 so that an image is displayed on the display device 300 and controls the aperture mechanism 205 to adjust the light amount incident on the light guide cable 106.

If the hard key 400 is not connected (S16: NO), then the system controller 210 retrieves the default settings stored in the ROM 210B, and controls the signal processing unit 208 so that the display device 300 displays an image in accordance with the default settings. The aperture mechanism 205 is also controlled in accordance with the default settings (S24).

If the ID code transmitted from the hard key 400 does not coincide with any one of the registered ID code DID, control also proceeds to S24 where the amount of light as well as image display condition on the display device 300 are controlled in accordance with the default settings.

According to the above configuration, if a hard key 400 containing the ID code which is the same as the registration ID code stored in the battery back up RAM 210D is coupled to the connector 207, image displaying condition and light amount are set in accordance with the imaging parameter DDS stored in the battery back up RAM 210D. Therefore, if an operator has the hard key 400, even though another user users different settings, the operator having the hard key 400 can use the same settings as previously used by the user.

On the other hand, if the ID code stored in the hard key 400 does not coincide with the registration ID code or the hard key 400 is not coupled to the connector 207, the default settings are used. In this case, the same settings (i.e., the default settings) are initially used, and accordingly, an operator can change the settings, starting from the default setting, as he/she desires easily.

FIG. 8 is a flowchart illustrating a sub routine for monitoring connection/removal of the hard key 400 during the normal operation of the electronic endoscope system 1000.

The sub routine shown in FIG. 8 is executed periodically while the normal operation is executed.

In S32, the variable HK is set to 0. Then, in S36, it is determined whether the hard key 400 is coupled to the connector 207. If the hard key 400 is not coupled to the connector 207 (S36: NO), then control returns to the normal operation. At this stage, the settings currently used are not changed.

If the hard key 400 is coupled to the connector 207 (S36: YES), then it is determined whether the ID code stored in the hard key 400 coincides with the registration ID code DID stored in the battery back up RAM 210D (S38). If the ID code stored in the hard key 400 matches the registration ID code stored in the battery back up RAM 210D (S38: YES), the variable HK is set to 1 (S40), and control proceeds to S42 where the currently used settings are changed to the imaging parameters DDS stored in the battery back up RAM 210D.

If the ID code stored in the hard key 400 does not coincide with the registration ID code stored in the battery back up RAM 210D (S38: NO), the variable HK is not set to 1 (i.e., HK=0), and control returns to the normal operation without changing the settings.

According to the above configuration, even if the hard key 400 is coupled to the connector 207 during the normal operation, the settings (i.e., the imaging parameters) stored in the battery back up RAM 210D are retrieved, and image displaying condition on the display device 300 and the light amount are controlled in accordance with the retrieved imaging parameters DDS. If the hard key 400 is not coupled to the connector 207, even if the variable HK is set to 0, the currently used settings (but not the default settings) are used. Further, even if the hard key 400 were coupled to the connector 207, and is removed during the normal operation, the currently used settings are not changed to the default settings.

By operating the touch switches on the front panel 204, a parameter changing mode can be selected. The image screen 300A shown in FIG. 6 is displayed when the main unit 200 operates in the parameter changing mode.

FIG. 9 is a flowchart illustrating the parameter changing operation, which starts when the operation mode of the main unit 200 is changed to the parameter changing mode.

As described above, by operating the touch switches and/or operating the keyboard 214 when the image shown in FIG. 6 is displayed, the settings can be changed (SS0). The changed settings are temporarily stored in the RAM 210C.

Then, the system controller 210 determines whether the variable HK is equal to 1 (i.e., whether the correct hard key 400 is coupled to the connector 207) (S52). If the variable HK is equal to 1 (S52: YES), then the settings stored in the RAM 210C are transmitted to the battery back up RAM 210D (S54). In this operation, the previously stored settings are replaced with the settings transmitted from the RAM 210C. Then, the operation mode is changed to the normal operation mode (S56). In the normal operation, the new settings stored in the RAM 210C are used. If the variable HK is equal to 0 (S52: NO), the normal operation is executed (S56), in which the settings stored in the RAM 210C are used.

According to the above configuration, if a hard key 400 containing the ID code which coincides with the registration ID code stored in the battery back up RAM 210D is coupled to the connector 207, when the imaging parameters are changed, the changed settings are stored in the battery back up RAM 210D. However, if the hard key 400 is not coupled to the connector 207, or even though it is coupled, the stored ID code does not match the registration ID code stored in the battery back up RAM 210D, the changed settings are not stored in the battery back up RAM 210D. Thus, only the operator who has the hard key containing the ID code which coincides with the registration ID code stored in the battery back up RAM 210D can store the changed imaging parameters.

As described above, according to the first embodiment, by coupling the hard key 400, which contains the same ID code as the registration ID code stored in the battery back up RAM 210D, to the connector 207, the display device 300 displays an image in accordance with the stored image display settings DDS, and further, if the imaging parameters are changed, the new settings of the imaging parameters can be stored. Accordingly, the operator who has the hard key 400 containing the same ID code as the registration ID code can use the electronic endoscope system with his/her usual settings which have been stored in the battery back up RAM 210D only by coupling the hard key 400 to the connector 207. Further, the settings of the imaging parameters can be changed only by the operator who has the hard keys 400 containing the same ID code as the registration ID information.

In the first embodiment described above, only one set of imaging parameters are stored. The first embodiment can be modified so that a plurality of sets of imaging parameters are stored for a plurality of operators having hard keys, respectively. Such a configuration will be described as a second embodiment.

Second Embodiment

FIG. 10 schematically shows storage areas of the battery back up RAM 210D according to the second embodiment. As shown in FIG. 10, the battery back up RAM 210D has a first storage area a10 including a plurality of sections for storing a plurality of (from 1st to n-th) registration ID codes DID1–DIDn, and a second storage area a20 including a plurality of sections for storing a plurality of sets (from 1st to n-th) of imaging parameters DDS1–DDSn. The plurality of registration ID codes DID1–DIDn correspond to the plurality of sets of imaging parameters DDS1–DDSn, respectively.

In the second embodiments, there are a plurality of hard keys 400 containing different ID codes, which correspond to the plurality of registration ID codes DID1–DIDn stored in the battery back up RAM 210D.

FIG. 11 is a flowchart illustrating a main procedure of the electronic endoscope system 1000 according to the second embodiment. The main procedure starts when a main switch (not shown) of the main unit 200 is turned ON, and power is supplied to the circuits therein.

When the main unit 200 is powered ON, the CPU 210A performs an initialization operation (S62), during which a variable HK stored in the RAM 210C is set to zero (0). The variable HK represents presence/absence of the hard key 400. That is, when the hard key 400 is not connected, the variable HK equals 0, while when the hard key 400 has been connected, the variable HK equals 1.

In S64, the system controller 210 sends a command to the communication unit 206 to detect whether the hard key 400 is coupled to the connector 207. In response to the command, the communication unit 206 transmits a signal to the connector 207 requiring a response therefrom. Based on the absence/presence of the response from the hard key 400 via the connector 207, whether the hard key 400 is connected to the connector 207 is determined (S66).

If the hard key 400 responds, the communication unit 206 communicates with the hard key 400 to receive the ID code stored in the hard key 400, and transmits the received ID code to the system controller 210.

In S68, the system controller 210 determines whether the ID code transmitted from the hard key 400 is correct, i.e., the ID code coincides with one of the plurality of registration ID codes stored in the battery back up RAM 210D. If the ID code received from the hard key 400 coincides with one of the plurality of registration ID codes stored in the battery back up RAM 210D (S68: YES), the variable HK is set to 1 (S70), which represents a correct hard key 400 is coupled to the connector 207.

Next, the system controller 210 identifies one of the plurality of registration ID codes DID1–DIDn, which coincides with the ID code stores in the currently coupled hard key 400 (S72). Then, in S74, the system controller 210 reads out the imaging data corresponding to the identified registration ID code. For example, if the received ID code equals an registration ID code DIDk, then in S74, the imaging data DDSk is read out from the battery back up RAM 210D.

Then, the CPU 210A executes a normal operation, i.e., the CPU 210A controls, in accordance with the imaging data DDSk read out from the battery back up RAM 210D in S74, the signal processing unit 208 so that an image is displayed on the display device 300, and the aperture mechanism 205 to adjust the light amount incident on the light guide cable 106.

If the hard key 400 is not connected (S66: NO), then the system controller 210 retrieves the default settings of the imaging parameters stored in the ROM 210B, and controls the signal processing unit 208 so that the display device 300 displays an image in accordance with the default settings. The amount of light is also controlled in accordance with the default settings (S80).

If the ID code transmitted from the hard key 400 does not coincide with any one of the registered ID codes DID1–DIDn (S68: NO), control also proceeds to S80 where the amount of light as well as image display condition on the display device 300 are controlled in accordance with the default settings.

According to the above configuration, if a hard key 400, which contains the ID code corresponding to one of the plurality of registration ID codes, is coupled to the connector 207, image displaying condition and light amount are set in accordance with the imaging parameters corresponding to the ID code of the coupled hard key 400. Therefore, if operators have their own hard keys 400, even though another operator uses different settings, each operator can use his/her own settings which may be previously used by him/her, and stored in the battery back up RAM 210D.

On the other hand, if the ID code stored in the hard key 400 does not coincide with any one of the registration ID codes or the hard key 400 is not coupled to the connector 207, the default settings are used. Therefore, in this case, the same settings (i.e., the default settings) are initially used, and thus, an operator can usually change the settings from the same initial settings to ones he/she desires easily.

By operating the touch switches on the front panel 204, a parameter changing mode can be selected. In the parameter changing mode, the image displayed on the display device 300 is the same as that in the first embodiment (see FIG. 6).

FIG. 12 is a flowchart illustrating the parameter changing operation according to the second embodiment, which starts when the operation mode of the main unit 200 is changed to the parameter changing mode.

As described in connection with the first embodiment, by operating the touch switches and/or operating the keyboard 214, the settings of each parameters can be changed (S90). The changed settings are temporarily stored in the RAM 210C.

Then, the system controller 210 determines whether a hard key 400 is coupled to the connector 207 (S92). If the hard key 400 is coupled to the connector 207 (S92: YES), then the ID code stored in the hard key 400 is read out, and the settings stored in the RAM 210C are transmitted to the battery back up RAM 210D (S94) and stored in relation to a registration ID code that coincides with the ID code read out of the connected hard key 400. By this operation, the previously stored settings corresponding to the ID code of the hard key 400 are replaced with the settings stored in the RAM 210C. Then, the display condition and light amount are changed in accordance with the new settings stored in the RAM 210C (S100), and then the operation mode is changed to the normal operation mode (S102). If the hard key 400 is not connected (S92: NO), or the hard key 400 is connected but the ID code does not coincide with any one of the registration ID codes, then control directly proceeds to S100 for change the display condition and light amount in accordance with the settings stored in the RAM 210C (S100), and the operation mode is changed to the normal operation mode (S102).

According to the above configuration, if a hard key 400 containing the ID code which coincides with one of the plurality of registration ID codes stored in the battery back up RAM 210D is coupled to the connector 207, when the image display settings are changed, the changed settings are stored in the battery back up RAM 210D in relation to the ID code contained in the hard key 400. However, if the hard key 400 is not coupled to the connector 207, or even though it is coupled, the stored ID code does not match the registration ID codes stored in the battery back up RAM 210D, the changed settings are not stored in the battery back up RAM 210D. Thus, only the operators who have the hard keys containing the ID codes which match the registration ID codes stored in the battery back up RAM 210D can store the changed settings of the imaging parameters.

As described above, according to the second embodiment, by coupling the hard key 400, which contains the same ID code as one of the registration ID codes stored in the battery back up RAM 210D, to the connector 207, the display device 300 displays an image in accordance with the stored imaging parameters, and further, if the settings are changed, the new settings can be stored in the battery back up RAM 210D. Accordingly, the operators who have the hard keys 400 containing the ID codes which are the same as the registration ID codes can use the electronic endoscope system with their usual settings which have been stored in the battery back up RAM 210D only by coupling the hard key 400 to the connector 207. Further, the settings corresponding to a certain registration ID code are changed only by operators who have the hard keys 400 containing the corresponding ID code.

In the first and second embodiments, for storing the registration ID code(s) and image settings, a battery back up RAM 210D is employed. The invention is not limited to such a configuration, and another NMV, e.g., an EEPROM may be used instead of the battery back up RAM.

Third Embodiment

A third embodiment will be described with reference to FIGS. 13–16. The structure of the electronic endoscope is substantially the same as the first and second embodiments (see FIGS. 1–4), and description thereof will be omitted.

In the third embodiment, the RAM 210C stores first setting data DSD1. Further, the battery back up RAM 210D stores registration ID code DID and second setting data DSD2.

FIG. 13 schematically shows a storage area a30 of the RAM 210C for storing the first setting data DSD1. The first setting data includes enhancement parameter D1, color balance parameter D2, and brightness parameter D3.

FIG. 14 schematically shows a storage area a40 for storing the registration ID code DID, and another storage area a41 for storing the second setting data DSD2 of the battery back up RAM 210D.

The registration ID code DID is set corresponding to a specific hard key 400. That is, the hard key 400 contains ID code that is the same as the registration ID code. When the hard key 400 is coupled to the connector 207, the ID data code in the hard key 400 is transmitted to the communication unit 206.

The second setting data DSD2 includes a gamma value setting data D20, individual light amount data D21, shutter speed data D22 and hue setting data D23.

In the ROM 210B, default data for the first setting data DSD1 is stored in advance.

According to the third embodiment, the main unit 200 is operable in a normal operation mode for observing the image captured by the CCD 110 of the endoscope unit 100 and two parameter setting modes: a normal setting mode; and a special setting mode.

The normal setting mode is a mode in which an operator changes the settings of the first setting data. The special setting mode is a mode in which the second setting data DSD2 is changed when maintenance is performed. It should be noted that the second setting data DSD2 should not generally be changed by normal operators of the electronic endoscope system 1000, but should be changed by a person who performs maintenance of the electronic endoscope system 1000.

In the third embodiment, when the electronic endoscope system 1000 is powered ON, if the endoscope unit 100 is connected to the main unit 200, a image captured by the CCD 110 of the endoscope unit 100 is displayed on the display device 300. If the endoscope unit 100 is not connected to the main unit 200 when the endoscope system 1000 is turned ON, a color bar image is displayed on the display device 300.

By operating the touch switches on the front panel 204 appropriately, operation of the main unit 200 is switched to the normal setting mode. The changeable items in the normal setting mode are similar to those shown in FIG. 6, which are referred to as the first setting data in the third embodiment, and will be omitted.

The changed settings (i.e., the first setting data) are stored in the storage area a30 of the RAM 210C as shown in FIG. 13.

The system controller 210 controls the signal processing unit 208 so that the image is displayed on the display device 300 in accordance with the enhancement parameter D1 and the color balance parameter D2, and controls the aperture mechanism so that the amount of light directed to the light guide cable 106 is adjusted in accordance with the brightness parameter D3.

Next, the special setting mode will be described.

FIG. 15 shows an exemplary screen image displayed on the screen 300A of the display device 300 when the main unit 200 operates in the special setting mode. The operation mode of the main unit 200 is changed to the special setting mode when the hard key 400 is coupled to the connector 207.

As shown in FIG. 15, on a display screen 300A of the display device 300, changeable items and settings of each item are displayed. In FIG. 15, as the changeable parameters, "γ Level", "Diaphragm Step Table", "Shutter Speed" and "Color Step" are displayed.

The "γ Level" parameter represents a setting of the γ level (i.e., the gamma data D20). The Diaphragm Step Table represents a table defining differences of light amount between two subsequent diaphragm steps. The shutter speed parameter represents the shutter speed of the CCD 110 (i.e., the shutter speed data D22). The color step parameter represents values corresponding to the hue (i.e., the hue setting data D23).

In the example shown in FIG. 15, the "γ Level" parameter is set by a number, the "Diaphragm Step Table" is defined by assigning values on the right-hand side column representing a difference between two subsequent diaphragm steps to the numbers on the left-hand side column representing the diaphragm steps. For example, according to FIG. 15, the number of steps representing a difference of light amount between diaphragm steps +5 and +5 is set to "10", and that between diaphragm steps +3 and +4 is set to "05". The "Shutter Speed" parameter can also be set by a number, and the "Color Step" is defined by assigning a value for each of Red, Blue and Green components.

FIG. 16 is a flowchart illustrating a main procedure of the electronic endoscope system 1000 according to the third embodiment. The main procedure starts when a main switch (not shown) of the main unit 200 is turned ON, and power is supplied to the circuits therein.

When the main unit 200 is powered ON, the CPU 210A performs an initialization operation (S110).

In S112, the system controller 210 sends a command to the communication unit 206 to detect whether the hard key 400 is coupled to the connector 207. Then, the communication unit 206 transmits a signal to the connector 207 requiring a response therefrom. Based on the absence/presence of the response from the hard key 400, it is determined whether the hard key 400 is coupled to the connector 207 (S114).

If the hard key 400 responds, the communication unit 206 communicates with the hard key 400 to receive the ID code stored therein, and transmits the received ID code to the system controller 210.

In S116, the system controller 210 determines whether the ID code transmitted from the hard key 400 is correct, i.e., the ID code coincides with the registration ID code that is stored in the battery back up RAM 210D. If the ID code received from the hard key 400 coincides with the registration ID code stored in the battery back up RAM 210D (S116: YES), the operation mode of the main unit 200 is automatically changed to the special setting mode (S118). At this stage, the display device 300 displays the image as shown in FIG. 15 so that the operator can change the second setting data DSD2 (S120). The second setting data DSD2 can be changed by operating the touch switches of the front panel 204 and/or keyboard 214.

The changed second setting data DSD2 is then stored in the battery back up RAM 210D (S122).

Then, the CPU 210A controls the signal processing unit 208 and the aperture mechanism 205 in accordance with the first setting data DSD1 stored in the RAM 210C and the second setting data stored in the battery back up RAM 210D (S124), and control proceeds to S126 where the normal operation is executed.

If the hard key 400 is not connected (S114: NO), the maintenance is not being performed, and accordingly, control directly proceeds to the normal operation (S126).

If the hard key 400 is coupled to the connector 207 but the ID code transmitted from the hard key 400 does not coincide with the registered ID code Did (S116: NO), control also proceeds to S126.

According to the third embodiment, if a hard key 400 containing the ID code which coincides with the registration ID code is coupled to the connector 207, the operation mode of the main unit 200 is automatically and immediately changed to the special setting mode, and the image shown in FIG. 15 is displayed. Thus, only an operator having such a hard key 400 can change the second setting data, and the ordinary users cannot change the second setting data either intentionally or by mistake. Further, only by coupling the hard key 400 to the connector 207, the operation mode is automatically changed to the special setting mode. Therefore, maintenance operation can be performed quickly.

It should be noted that, in the third embodiment, the battery back up RAM 210C can be replaced with another non-volatile type memory such as an EEPROM.

The changeable parameters of the first and second setting data are not limited to the above-described ones, but can be modified in various ways.

Further, setting parameters need not be limited to ones related to the image display condition and light amount, but various type of settings may be made changeable in the similar manner.

It should be noted that a similar function may be achieved with use of a memory card. However, in such a case, a card slot should be provided in the main unit 200. According to the above-described embodiments, since the hard key is used, and further, the hard key is connected to the communication port which is generally provided for connecting external devices such as computers. Therefore, in comparison to the case where the memory card is used, the system can be configured at less cost since no extra port (i.e., the card slot) is provided only for the managing the imaging parameters.

The present disclosure relates to the subject matters contained in Japanese Patent Applications No. HEI 10-316015 and HEI 10-316301, both filed on Nov. 6, 1998, which are expressly incorporated herein by reference in their entireties.

What is claimed is:

1. An electronic endoscope system, including an endoscope unit provided with an image capturing device, said image capturing device outputting an image signal representing a captured image; a video processing unit for processing the image signal output by said image capturing device; and a display device that displays an image in accordance with the image signal processed by said video processing unit, said video processing unit including:
an image display condition controlling system that controls a displaying condition of an image on said display device, the displaying condition being determined in accordance with displaying parameters;
a changing device for changing said displaying parameters;
a memory for storing at least one registration ID (identification) code and the displaying parameters,
said endoscope system further comprising an ID code input member, which inputs an ID code instrinsic to said ID code input member, to said video processing unit,
said video processing unit further including:
a discriminating system which discriminates whether the ID code input from said ID code input member coincides with said at least one registration ID code;

a controller that controls said image display controlling system to adjust the displaying condition in accordance with the displaying parameters stored in said memory when said ID code input from said ID code input member coincides with said at least one registration ID code, said controller controlling said image display condition controlling system to adjust the displaying condition in accordance with a predetermined reference displaying parameters when said ID code input from said ID code input member does not coincide with said at least one registration ID code.

2. The electronic endoscope system according to claim 1, said controller controlling said display condition controlling system to adjust the displaying condition in accordance with the predetermined reference displaying parameters when said ID code is not input from said ID code input member.

3. The electronic endoscope system according to claim 1, wherein said controller stores the displaying parameters set to said display condition when said ID code input from said ID code input member coincides with said at least one registration ID code.

4. The electronic endoscope system according to claim 3, wherein said controller stores the displaying parameters in said memory when the displaying parameters are changed by said changing device.

5. The electronic endoscope system according to claim 1, wherein said ID code input member comprises a hard key to which stores an ID code assigned thereto, wherein said video processing unit further comprising a communication system which is detachably coupled to said hard key, wherein said discriminating system transmits a request via said communication system to said hard key for response, said hard key transmits the ID code storing therein to said discrimination system via said communication system in response to said request.

6. The electronic endoscope system according to claim 5, wherein said controller controls said image display condition controlling system to adjust the displaying condition in accordance with predetermined reference displaying parameters when said communication system does not receive a response from said hard key.

7. The electronic endoscope system according to claim 1, wherein said displaying parameters include at least one of a parameter for setting color balance of an image and a parameter for setting an enhancement of a displayed image.

8. The electronic endoscope system according to claim 1, further comprising a light source for emitting light, and a light guide cable for directing the light emitted by said light source to said endoscope unit, said displaying parameters include a parameter for setting light amount, said controller controls the amount of light guided by said light guide cable in accordance with the parameter for setting light amount.

9. An electronic endoscope system, including an endoscope unit provided with an image capturing device, said image capturing device outputting an image signal representing a captured image; a video processing unit for processing the image signal output by said image capturing device; and a display device that displays an image in accordance with the image signal processed by said video processing unit, said video processing unit including:
an image display condition controlling system that controls a displaying condition of an image on said display device, the displaying condition being determined in accordance with displaying parameters;
a changing device for changing said displaying parameters;
a memory for storing a plurality of registration ID (identification) codes and a plurality of sets of displaying parameters, said plurality of sets corresponding to said plurality of registration ID codes, respectively,
said endoscope system further comprising and ID code input member, which inputs an ID code intrinsic to said ID code input member, to said video processing unit,
said video processing unit further including:
a discriminating system which discriminates whether the ID code input from said ID code input member coincides with one of said plurality of registration ID codes;
a controller that controls said display condition controlling system to adjust the displaying condition in accordance with one of said plurality of sets of displaying parameters stored in said memory and corresponding to said ID code input from said ID code input member when said ID code input from said ID code input member coincides with one of said plurality of sets of registration ID codes, said controller controlling said display condition controlling system to adjust the displaying condition in accordance with a predetermined reference displaying parameters when said ID code input from said ID code input member does not coincide with any one of said plurality of registration ID codes.

10. The electronic endoscope system according to claim 9, said controller controlling said display condition controlling system to adjust the displaying condition in accordance with the predetermined reference displaying parameters when said ID code is not input from said ID code input member.

11. The electronic endoscope system according to claim 9, wherein said controller stores the displaying parameters set to said display condition in relation to a registration ID code which coincides with said ID code input from said ID code input member when said ID code input from said ID code input member coincides with said one of said plurality of registration ID codes.

12. The electronic endoscope system according to calim 11, wherein said controller stores the displaying parameters in said memory when the displaying parameters are changed by said changing device.

13. The electronic endoscope system according to claim 9, wherein said ID code input member comprises a hard key to which stores an ID code assigned thereto, wherein said video processing unit further comprising a communication system which is detachably coupled to said hard key, wherein said discriminating system transmits a request via said communication system to said hard key for response, said hard key transmits the ID code storing therein to said discrimination system via said communication system in response to said request.

14. The electronic endoscope system according to claim 13, wherein said controller controls said image display condition controlling system to adjust the displaying condition in accordance with predetermined reference displaying parameters when said communication system does not receive a response from said hard key.

15. The electronic endoscope system according to claim 9, wherein said displaying parameters include at least one of a parameter for setting color balance of an image and a parameter for setting an enhancement of a displayed image.

16. The electronic endoscope system according to claim 9, further comprising a light source for emitting light, and a light guide cable for directing the light emitted by said light source to said endoscope unit, said displaying parameters include a parameter for setting light amount, said controller controls the amount of light guided by said light guide cable in accordance with the parameter for setting light amount.

17. An electronic endoscope system which operates in accordance with setting information, said setting information including at least first setting parameters and second setting parameters, said electronic endoscope system operable either in a first setting mode where said first setting parameters are changed or in a second setting mode where said second setting parameters are changed, said electronic endoscope system comprising:

a memory for storing a registration ID (identification) code;

an ID code input member stores an ID code intrinsic to said ID code input member, a discriminating system, said ID code intrinsic to said ID code input member being input to said discriminating system, said discriminating system discriminating whether the ID code received from said ID code input member coincides with said registration ID code;

a controller that allows said endoscope system to operate in said second setting mode only when said discriminating system has received said ID code from said ID code input member and said ID code coincides with said registration ID code.

18. The electronic endoscope system according to claim 17, wherein said controller controls said endoscope system to operate in said second setting mode when said discriminating system has received said ID code from said ID code input member and said ID code coincides with said registration ID code.

19. The electronic endoscope system according to claim 17, further comprising a display device, and wherein said setting information includes display condition setting parameters for setting a display condition of an image on said display device.

20. The electronic endoscope system according to claim 17, wherein said ID code input member comprises a hard key which stores an ID code assigned thereto, wherein discriminating system further comprising a communication system to which said hard key is detachably coupled, wherein said communication system transmits a request to said hard key for response, said hard key transmitting the ID code storing therein to said communication system in response to said request.

21. The electronic endoscope system according to claim 20, wherein said controller inhibits said electronic endoscope system from operating in said second setting mode when said communication system does not receive a response from said hard key.

22. The electronic endoscope system according to claim 19, wherein said first setting parameters include at least one of a parameter for setting color balance of an image and a parameter for setting an enhancement of a displayed image.

23. The electronic endoscope system according to claim 19, further comprising a light source for emitting light, and a light guide cable for directing the light emitted by said light source to said endoscope unit, said display condition setting parameters including a parameter for setting light amount, said controller controlling the amount of light guided by said light guide cable in accordance with the parameter for setting light amount.

24. The electronic endoscope system according to claim 19, wherein said second setting parameters include at least one of a gamma level setting parameter for setting gamma correction level for said display and a parameter for setting hue of a displayed image.

25. The electronic endoscope system according to claim 19, further comprising an endoscope unit provided with an image capturing device, and wherein said second setting parameters include a parameter for setting a shutter speed for said image capturing device.

* * * * *